(12) United States Patent
Judkins et al.

(10) Patent No.: US 7,230,114 B2
(45) Date of Patent: Jun. 12, 2007

(54) INTERMEDIATES FOR PREPARING NEURAMINIDASE INHIBITOR CONJUGATES

(75) Inventors: Brian David Judkins, Hertfordshire (GB); Simon John Fawcett MacDonald, Hertfordshire (GB); Derek Anthony Demaine, Hertfordshire (GB); Graham George Adam Inglis, Hertfordshire (GB); Julie Nicole Hamblin, Hertfordshire (GB)

(73) Assignee: Biota Scientific Management Pty Ltd, Melbourne (AU)

( * ) Notice: Subject to any disclaimer, the term of this patent is extended or adjusted under 35 U.S.C. 154(b) by 0 days.

(21) Appl. No.: 10/488,791

(22) PCT Filed: Aug. 30, 2002

(86) PCT No.: PCT/AU02/01187

§ 371 (c)(1), (2), (4) Date: Sep. 27, 2004

(87) PCT Pub. No.: WO03/022841

PCT Pub. Date: Mar. 20, 2003

(65) Prior Publication Data

US 2005/0032853 A1 Feb. 10, 2005

(30) Foreign Application Priority Data

Sep. 7, 2001 (AU) .................................. PR 7574

(51) Int. Cl.
*C07D 233/00* (2006.01)
(52) U.S. Cl. .................... 548/311.1; 548/517; 549/414
(58) Field of Classification Search ............... 549/414; 548/311.1, 517
See application file for complete search history.

(56) References Cited

U.S. PATENT DOCUMENTS 5,919,819 A 7/1999 Andrews et al.

6,242,582 B1 6/2001 Reece et al.

OTHER PUBLICATIONS

Reece, PA et al 'Preparaton of poly(neuraminic acids) as influenza virus neuraminidase inhibitors' CA 129:28172 (1999).*
Chemical Abstracts, Abstract 132: 23155 [& Andrews, D.M., et al: "Synthesis and influenza virus sialidase inhibitory activity of analogues of 4-guanidino-Neu5Ac2en (Zanamivir) modified in the glycerol side-chain"; European Journal of Medicinal Chemistry (1999), 34 (7&8), 563-574] See Chemical Abstracts Registry Nos. 252061-43-1, 232061-44-2, 252061-47-8, 252061-50-0.
Chemical Abstracts, Abstract 128:12878 [& AU 199737858 (723994) B2 (Sankyo Company, Limited) Sep. 7, 2000] See Chemical Abstracts Registry Nos. 203733-75-9, 203733-77-1, 203733-80-6, 203733-84-0, 203733-88-4, 203733-92-0, 203733-96-4.

* cited by examiner

*Primary Examiner*—Amelia A. Owens
(74) *Attorney, Agent, or Firm*—Foley & Lardner LLP

(57) ABSTRACT

Compounds of formula (I), methods for their preparation and their use in the manufacture of neuraminidase inhibitor conjugates. Wherein R represents as carboxylic acid protecting group; $P_1$ and $P_2$ can be the same or different and are selected from amine protecting groups; $P_3$ represents a protecting group for 1, 2 diols; and LG represents a leaving group

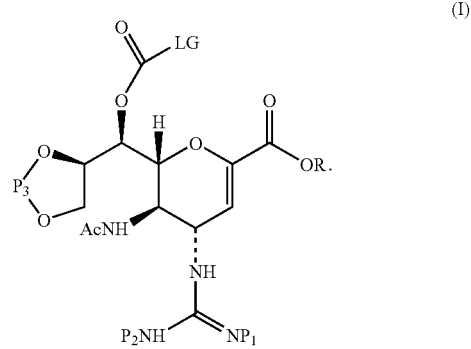

(I)

36 Claims, No Drawings

INTERMEDIATES FOR PREPARING NEURAMINIDASE INHIBITOR CONJUGATES

The present invention relates to novel compounds, methods for their preparation and their use in the manufacture of neuraminidase inhibitor conjugates.

Dimeric compounds and their use as neuraminidase inhibitors have been disclosed in WO00/55149. Polymeric compounds and their use as neuraminidase inhibitors have been disclosed in WO98/21243. In WO00/55149, it was shown that when two neuraminidase-binding compounds are suitably linked together through a region of the molecule that is not involved in binding to the active site, the resultant dimers have enhanced anti-viral activity. Eur. J. Med. Chem 34 (1999) 563–574 discloses the synthesis and influenza virus sialidase inhibitory action of an analogue series of 4-guanidino-Neu5Ac2en (zanamivir) modified in the glycerol side chain.

In WO00/55149, compound 7 is described as a useful precursor to certain dimeric neuraminidase inhibitors.

Compound (7)

[Chemical structure of Compound (7): showing $H_2N(CH_2)_6NH$ group, HO, HO, AcHN, CO$_2$H, and guanidino (HN=C(NH$_2$)NH–) substituents on a dihydropyran ring]

We have found that in a first aspect the invention provides compounds of formula (I):

(I)

[Chemical structure of formula (I): showing LG, OR, $P_3$, AcNH, $P_2NH$, $NP_1$ substituents on a dihydropyran ring with carbonate linker]

wherein R represents a carboxylic acid protecting group;
$P_1$ and $P_2$ can be the same or different and are selected from amine protecting groups;
$P_3$ represents a protecting group for 1,2 diols; and
LG represents a leaving group, for example, para-nitrophenol or a derivative thereof, halide, imidazole or N-hydroxysuccinimide.

Preferably R is $C_{1-6}$ alkyl, diphenylmethane or an appropriate protecting group selected by one skilled in the art from common carboxylic acid protecting groups such as those listed in "Protective Groups in Organic Synthesis," T W Greene and P G M Wuts 1999 ($3^{rd}$ edition), Wiley.

When used herein an alkyl group can be straight, branched or cyclic for example methyl, ethyl, propyl, isopropyl, butyl, t-butyl, pentyl, hexyl or cyclohexyl, preferably methyl or t-butyl.

Common amine protecting groups are as those listed in "Protective Groups in Organic Synthesis," T W Greene and P G M Wuts 1999 ($3^{rd}$ edition), Wiley, preferably a t-butoxycarbonyl (Boc) group.

Protecting groups for 1,2 diols are CO (a cyclic carbonate) or CHMe (a methyl acetal) or an appropriate protecting group selected by one skilled in the art from common 1,2 diol protecting groups such as those listed in "Protective Groups in Organic Synthesis," T W Greene and P G M Wuts 1999 ($3^{rd}$ edition), Wiley. Preferably $P_3$ represents CO or CHMe.

Other leaving groups will be known to the person skilled in the art for the preparation of carbamates.

Even more preferably R is methyl or diphenylmethane, $P_1$ and $P_2$ are Boc, $P_3$ is CO and LG is para-nitrophenol.

Compounds of the present invention offer a significant advantage in the rapid preparation of large numbers of neuraminidase inhibitor conjugates, specifically those disclosed in WO 00/55149. Compounds of the present invention provide a common intermediate from which a large number of neuraminidase inhibitor conjugates can be prepared using different "linking groups" many of which are commercially available. Using a common intermediate allows flexibility and the ability to produce large numbers of compound quickly.

Compounds of formula (I) may be useful in the preparation of compound libraries comprising at least 2, e.g. 5 to 1000, compounds, preferably 10 to 100 compounds. Compound libraries may be prepared by "split and mix" approach or by multiple parallel synthesis using either solution phase or solid phase chemistry, by process known in the art.

A second aspect of the invention is the use of compounds of formula (I) in the preparation of neuraminidase inhibitor conjugates, specifically those disclosed in WO 00/55149.

A third aspect of the invention is the process for the preparation of neuraminidase inhibitor conjugates, specifically those disclosed WO00/55149 comprising the use of compounds of formula (I).

A further aspect of the invention is neuraminidase inhibitor conjugates, specifically those disclosed in WO00/55149, prepared using compounds of formula (I).

WO00/55149 and WO98/21243 are incorporated by reference as if each individual publication were specifically and individually indicated to be incorporated by reference herein as though fully set forth. Specifically the generic formula of the neuraminidase inhibitor conjugates are incorporated herein.

Compounds of formula (I) can be prepared by reaction of compounds of formula (III);

(III)

[Chemical structure of formula (III): showing OH, OR, $P_3$, AcNH, $P_2NH$, $NP_1$ substituents on a dihydropyran ring]

wherein $P_1$, $P_2$, $P_3$ and R are as described for compounds of formula (I), with compounds of formula (II);

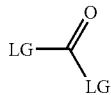

wherein each LG is independently as described for compounds of formula (I), in a solvent, and a base.

Preferably the base used is a tertiary amine, for example dimethylaminopyridine (DMAP), 4-pyrrolidinopyridine or 1,8-diazabicyclo[5.4.0]undec-7-ene, more preferably DMAP.

Preferably at least two equivalents of base to compound of formula (III) are used.

Preferably the solvent is pyridine or a pyridine type solvent.

Preferably the reaction should be carried out in the absence of water, for example by azetroping the starting materials, or drying in an oven prior to carrying out the reaction.

For example compounds of formula (II) may be symmetrical or unsymmetrical e.g. p-nitrophenylchloroformate.

Compounds of formula (III) can be prepared by reaction of compounds of formula (IV);

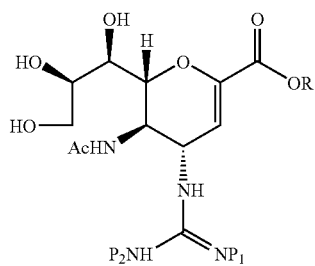

wherein $P_1$, $P_2$ and R are as described for compounds of formula (1), with carbonyldiimidazole (CDI) or phosgene or other phosgene equivalents.

Compounds of formula (IV) wherein R is diphenylmethane are known in the literature, J Med Chem 1998, 41, 787–797.

Neuraminidase inhibitor conjugates of formula (V);

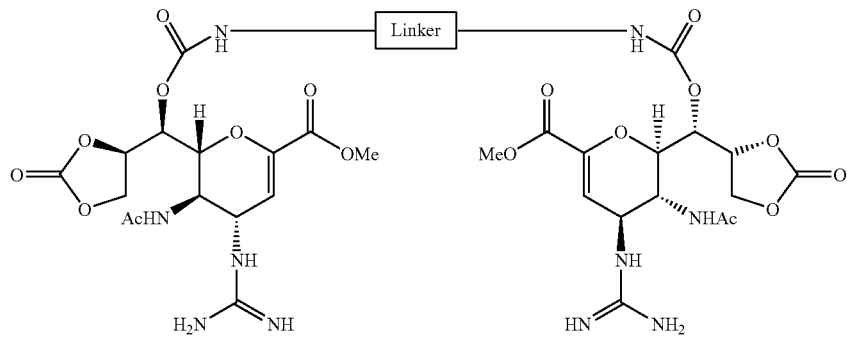

may be prepared by reacting compounds of formula (I) with compounds of formula (VI);

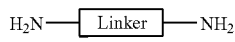

in solvent, for example pyridine, and in the presence of base, for example DMAP, followed if necessary by deprotection.

Methods of deprotecting the amine and ester groups will be well known to the person skilled in the art.

When used herein halide represents a fluoro, chloro, bromo or iodo group.

Compounds of formula (V) can be tested for neuraminidase activity by methods known in the art for example by plaque assays, Hayden et al. (Antimicrobial. Agents Chemother., 1980, 17, 865).

The invention will now be described in detail by way of reference to the following non-limiting examples.

Examples 1 and 2 disclose the preparation of compounds of formula (I). Example 3 describes the preparation of a neuraminidase inhibitor conjugate of formula (V).

Abbreviations used herein are
DPM—diphenylmethane
SPE—solid phase extraction.
DMAP—4-dimethylaminopyridine
BOC—t-butoxycarbonyl
EtOAc—ethyl acetate
DCM—dichloromethane
THF—tetrahydrofuran
CDI—1,1'-carbonyldiimidazole
LC/MS liquid chromatography mass spectrometry.

EXAMPLE 1

Intermediate 1 Benzhydryl (2R,3R,4S)-3-(acetylamino)-4-({[(tert-butoxycarbonyl)amino][(tert-butoxycarbonyl)imino]methyl}amino)-2-{(S)-hydroxy[(4R)-2-oxo-1,3-dioxolan-4-yl]methyl}-3,4-dihydro-2H-pyran-6-carboxylate

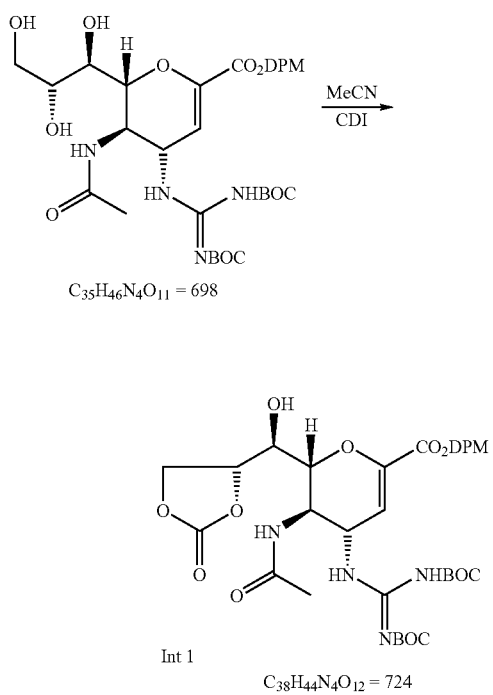

Benzhydryl (2R,3R,4S)-3-(acetylamino)-4-({(E)-[(tert-butoxycarbonyl)amino][(tert-butoxycarbonyl)imino]methyl}amino)-2-[(1R,2R)-1,2,3-trihydroxypropyl]-3,4-dihydro-2H-pyran-6-carboxylate (see J. Med. Chem. 1998, 41, 787–797) (12.38 g; 17.7 mmoles) was dissolved in dry acetonitrile (130 ml) under nitrogen at room temperature. The solution was stirred and 1,1'-carbonyldiimidazole (2.87 g; 17.7 mmoles) was added. After 16 hours LC/MS showed the presence of starting triol so further 1,1'-carbonyldiimidazole (total of 0.493 g; 3 mmoles) was added. After a few hours LC/MS showed no triol present. The solvent was evaporated and the residue flash columned on silica, eluting with 1:1 ethyl acetate/40–60 petroleum ether. Fractions containing wanted product were evaporated then taken up in dichloromethane, dried with sodium sulphate, filtered and evaporated to give Intermediate 1 as an off white solid (11.05 g; 86%).

LC/MS (Blue method) MH$^+$=725, T$_{ret}$=4.09 minutes.

EXAMPLE 1

Benzhydryl (2R,3R,4S)-3-(acetylamino)-4-({(E)-[(tert-butoxycarbonyl)amino][(tert-butoxycarbonyl)imino]methyl}amino)-2-{(S)-{[(4-nitrophenoxy)carbonyl]oxy}[(4R)-2-oxo-1,3-dioxolan-4-yl]methyl}-3,4-dihydro-2H-pyran-6-carboxylate

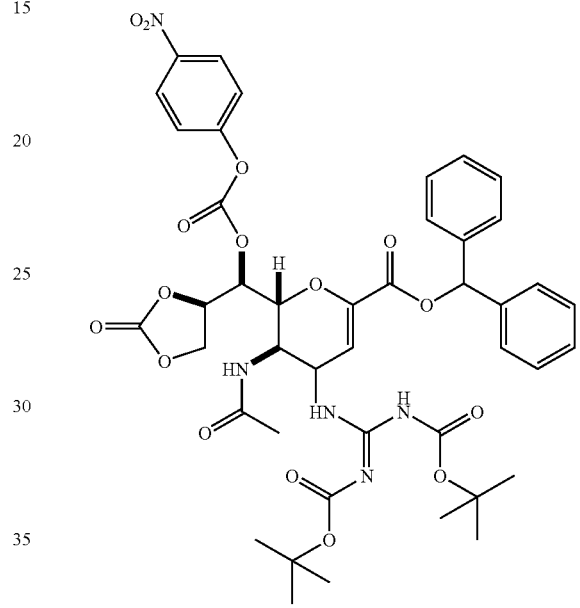

A solution of benzhydryl (2R,3R,4S)-3-(acetylamino)4-({[(tert-butoxycarbonyl)amino][(tert-butoxycarbonyl)imino]methyl}amino)-2-{(S)-hydroxy[(4R)-2-oxo-1,3-dioxolan-4-yl]methyl}-3,4-dihydro-2H-pyran-6-carboxylate (Intermediate 1)(143 mg, 0.197 mmol) in dry pyridine (3 ml) containing 4-dimethylaminopyridine (120 mg, 0.982 mmol) was treated with 4-nitrophenylchloroformate (199 mg, 0.987 mmol) at 22° C. The mixture was stirred at 22° C. For 17 h, then the pyridine removed in vacuo. The residue was purified by SPE chromatography (5 g cartridge) eluting with cyclohexane-ethyl acetate (4:1–2:1) to afford Example 1 as a pale yellow gum (99 mg, 56%).

NMR δ(CDCl$_3$) 11.30 (1H brd, NH), 8.62 (1H brd, NH), 8.23 (2H, AA'BB', aromatic CH's), 7.52 (2H, AA'BB', aromatic CH's), 7.43–7.30 (10Hm, aromatic CH's), 6.95 (1Hs, CH), 6.76 (1H brd, NH), 6.05 (1Hd, =CH), 5.56 (1Hdd, CH), 5.22 (1Hdt, CH), 5.00 (1Hdt, CH), 4.72 (1Hdd, CH), 4.59 (1Hdd, CH), 4.48 (1Hq, CH), 4.25 (1Hdd, CH), 1.92 (3Hs, CH3), 1.48 (9Hs, tert butyl), and 1.43 (9Hs, tert butyl).

LC/MS R$_1$=4.19 min. (MH$^+$=890, MH$^-$=888)

EXAMPLE 2

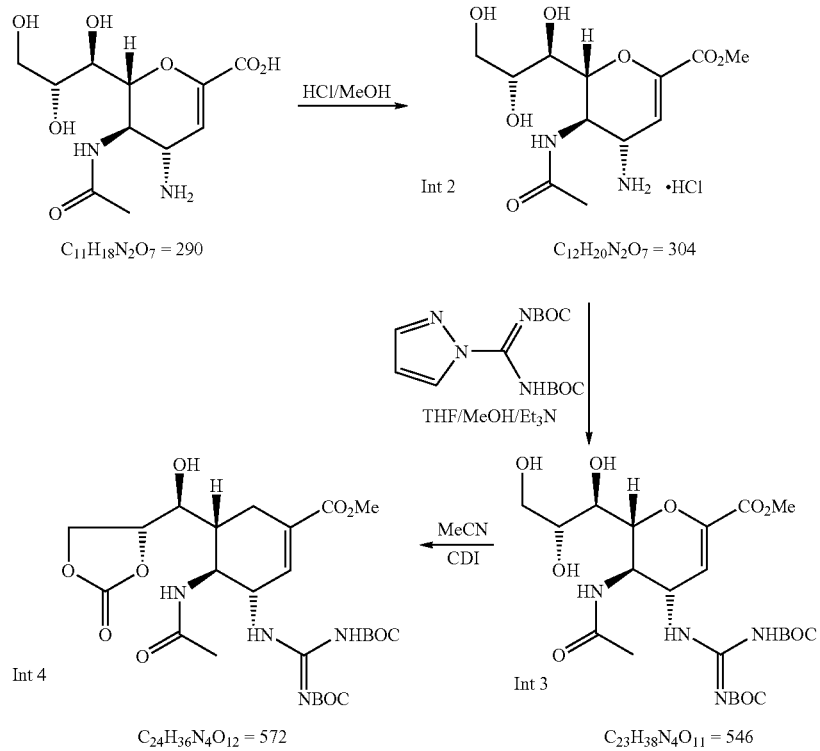

Intermediate 2 Methyl (2R,3R,4S)-3-(acetylamino)-4-amino-2-[(1R,2R)-1,2,3-trihydroxypropyl]-3,4-dihydro-2H-pyran-6-carboxylate hydrochloride Acetyl chloride (75 ml; 1.05 mole) was added drop-wise with stirring to methanol (7500 ml) at 0–5° C. under nitrogen. The mixture was stirred at this temperature for a further 15 minutes then held at approximately 10° C. as (2R,3R,4S)-3-(acetylamino)4-amino-2-[(1R,2R)-1,2,3-trihydroxypropyl]-3,4-dihydro-2H-pyran-6-carboxylic acid trihydrate (see J. Med. Chem. 1998, 41, 787–797) (250 g; 726 mmoles) was added in portions. The mixture was stirred at approximately 60° C. for 5 hours then cooled to approximately 20° C. and stirred at this temperature overnight. The solvent was removed and the residue twice evaporated down again with methanol (2×500 ml) to give a mixture of a foam and gum. This was re-dissolved in methanol (~1000 ml), evaporated and the residue then triturated with DCM and re-evaporated. The trituration DCM process was repeated. The residue was dried overnight in a vacuum-oven at approximately 30° C., crushed and then dried overnight again to give Intermediate 2 as a white powder (264.2 g).

LC/MS (Orange Method) MH$^+$=305, T$_{ret}$=0.54 minutes.

Intermediate 3 Methyl (2R,3R,4S)-3-(acetylamino)-4-({[(tert-butoxycarbonyl)amino][(tert-butoxycarbonyl)imino]methyl}amino)-2-[(1R,2R)-1,2,3-trihydroxypropyl]-3,4-dihydro-2H-pyran-6-carboxylate The amino ester hydrochloride Intermediate 2 (211.6 g; 0.62 mole) was added portion-wise to methanol (2100 ml) stirring under nitrogen in a 10 litre reactor to give a pale brown solution. THF (2100 ml) was added. Triethylamine (86.5 ml; 0.62 mole) was added drop-wise with stirring and then a solution of N,N'-bis-t-butyloxycarbonyl-1-guanylpyrazole (201.3 g; 0.649 mmole) in THF (2100 ml) was added drop-wise, fairly quickly, maintaining the reaction temperature at approximately 22° C. The mixture was stirred under nitrogen at approximately 22° C. for 45 hours then filtered to remove a small amount of solid and the filtrate evaporated to dryness. After standing overnight the gummy yellow residue was triturated with ethyl acetate (2500 ml) by rotation on rotary evaporator to give a fine white solid which was filtered off. The filtrate was evaporated down and dried under high vacuum to give a foam (~333 g). The foam was dissolved in 3% methanol/DCM (~700 ml) and purified on a 2.5 kg Biotage column pre-conditioned in and eluted with 3% methanol/DCM. The purest fractions were combined and evaporated then dried at approximately 30° C. to give Intermediate 3 as a white solid (192.8 g; 49.4% yield corrected for the presence of pyrazole). NMR showed the presence of ~54 mole % pyrazole (~13% by weight).

LC/MS (Orange Method) MH$^+$=547, T$_{ret}$=5.07 minutes.

Intermediate 4 methyl (2R,3R,4S)-3-(acetylamino)-4-({[(tert-butoxycarbonyl)amino][(tert-butoxycarbonyl)imino]methyl}amino)-2-{(S)-hydroxy[4R)-2-oxo-1,3-dioxolan-4-yl]methyl}-3,4-dihydro-2H-pyran-6-carboxylate Intermediate 3 (423.2 g; ca 0.77 mole) (contaminated with ~13% pyrazole), was dissolved in dry acetonitrile (4750 ml) and stirred under nitrogen in a 10 litre reactor. CDI (135.6 g; 0.84 mole) was added portion-wise using circulator to control the slight exotherm and maintain the reaction temperature at approximately 22° C. The mixture was stirred at this temperature under nitrogen overnight. After 22 hours the solvent was removed and the residual yellow gum was dissolved in ethyl acetate (3500 ml) and returned to the reactor. The solution was washed in the reactor twice with dilute hydrochloric acid (2×1250 ml; 1M), then once with water (1000 ml), then once with brine (800 ml). The solution was dried over magnesium sulphate, filtered, evaporated and dried in high vacuum to give a white foam (378 g). The foam was dissolved in DCM (~1000 ml) and the solution applied in two batches to a 2.5 kg Biotage column preconditioned in and eluted with 1:1 hexane/ethyl acetate to give, after evaporation and drying, Intermediate 4 as a white solid (total 292.1 g; ~76% based on corrected amount of starting material).

LC/MS (Orange Method) MH$^+$=573, T$_{ret}$=5.85 minutes.

EXAMPLE 2

Methyl (2R,3R,4S)-3-(acetylamino)-4-({(E)-[(tert-butoxycarbonyl)amino][(tert-butoxycarbonyl)imino]methyl}amino)-2-{(S)-{[(4-nitrophenoxy)carbonyl]oxy}[(4R)-2-oxo-1,3-dioxolan-4-yl]methyl}-3,4-dihydro-2H-pyran-6-carboxylate

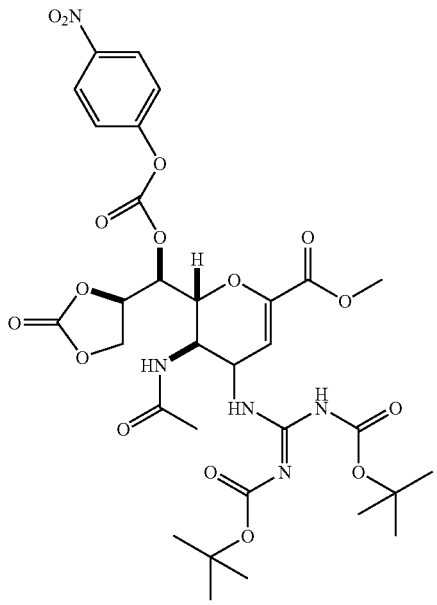

A solution of methyl (2R,3R,4S)-3-(acetylamino)-4-({[(tert-butoxycarbonyl)amino][(tert-butoxycarbonyl)imino]methyl}amino)-2-{(S)-hydroxy[(4R)-2-oxo-1,3-dioxolan-4-yl]methyl}-3,4-dihydro-2H-pyran-6-carboxylate (113 mg, 0.197 mmol) in dry pyridine (3 ml) containing 4-dimethylaminopyridine (120 mg, 0.982 mmol) was treated with 4-nitrophenylchloroformate (199 mg, 0.987 mmol) at 22° C. The mixture was stirred at 22° C. For 17 h, then the pyridine removed in vacuo. The residue was purified by SPE chromatography (5 g cartridge) eluting with cyclohexane-ethyl acetate (4:1–2:1) to afford Example 2 as a pale yellow gum (96 mg, 66%).

NMR δ(CDCl$_3$) 11.3 (1Hs, NH), 8.58 (1H brd, NH), 8.26 (2H, AA'BB', aromatic CH's), 7.56 (2H, AA'BB', aromatic CH's), 6.82 (1H brd, NH), 5.93 (1Hd, =CH), 5.54 (1Hdd, CH), 5.20 (1Hdt, CH), 5.10 (1Hdt, CH), 4.78 (2Hm, 2×CH), 4.44 (1H brq, CH), 4.28 (1Hdd, CH), 3.82 (3Hs CH3), 1.91 (3Hs, CH3), and 1.48 (18Hs, 2×tert butyl). LCMS R$_1$=3.87 min. (MH$^+$=738, MH$^-$=736)

EXAMPLE 3

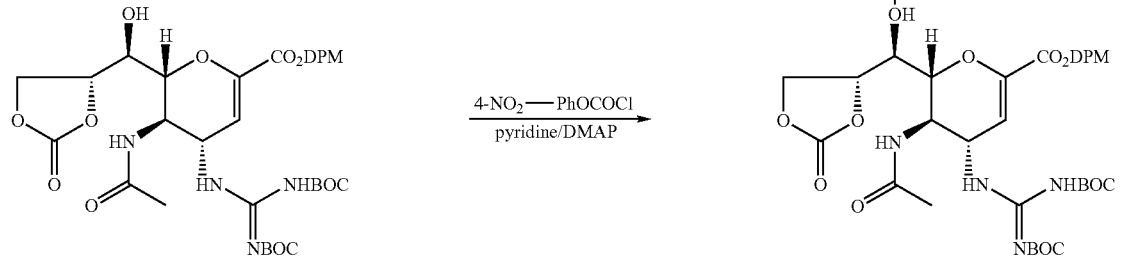

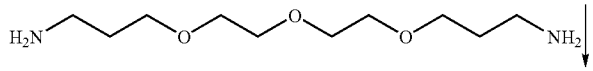

-continued

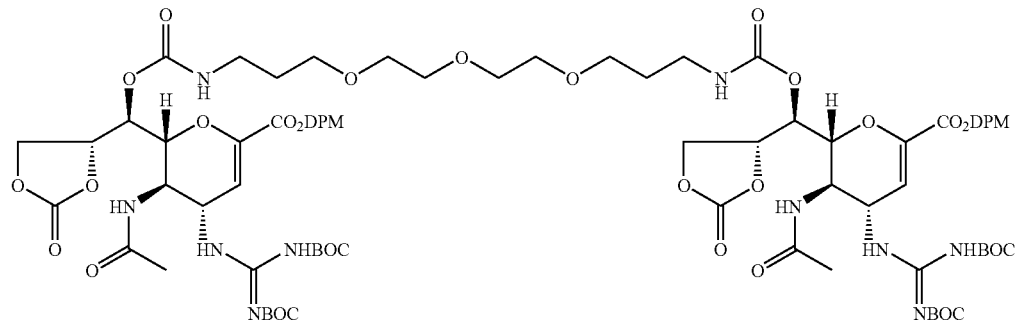

$C_{84}H_{108}N_{10}O_{29} = 1720$

The benzhydryl (2R,3R,4S)-3-(acetylamino)$_4$-({[(tert-butoxycarbonyl)amino][(tert-butoxycarbonyl)imino]methyl}amino)-2-{(S)hydroxy[(4R)-2-oxo-1,3-dioxolan-4-yl]methyl}-3,4-dihydro-2H-pyran-6-carboxylate (0.4 g; 0.55 mmole) was azeotroped 4 times from dry toluene and the dried solid was dissolved in molecular sieve-dried pyridine (1.6 ml). The solution was treated with 4-dimethylaminopyridine (0.17 g; 1.4 mmoles). To this was added 4-nitrophenylchloroformate (0.12 g; 0.6 mmole) under nitrogen. A slight exotherm occurred, the temperature rising from 24° C. to 27° C. The mixture was stirred at room temperature for 3 hours after which time LC/MS showed the absence of starting material and the presence of the nitrophenylcarbonate (Example 1) MH$^+$=890.

To this mixture was added 4,7,10-trioxa-1,13-tridecanediamine (60.7 mg; 0.276 mmole) in dry pyridine (1 ml). The resulting mixture was stirred at room temperature for 3 hours after which time LCMS showed the absence of the nitro compound 2 and the presence of product 3 at (M+2H$^+$)/2=861. Volatiles were removed in vacuo at 40° C. and the resulting orange oil was applied to a 10 g Si SPE cartridge eluted with DCM(5×), ether(5×) and EtOAc(5×). The product eluted in the EtOAc fractions as a white solid (0.2 g; 22%).

The product may be deprotected using standard techniques.

N.B. The 4-nitrophenylchloroformate should be white with no trace of yellow colour.

LC/MS Details-Blue Method
Micromass Platform II mass spectrometer operating in positive ion electrospray mode,
mass range 100–1000 amu.
Column: 3.3 cm×4.6 mm ID, 3 μm ABZ+PLUS
Flow Rate: 3 ml/min
Injection Volume: 5 μl
Solvent A: 95% acetonitrile+0.05% formic acid
Solvent B: 0.1% formic acid+10 mMolar ammonium acetate
Gradient: 0% A/0.7 min, 0–100% A/3.5 min, 100% A/1.1 min, 100–0% A/0.2 min LC/MS Details-Orange Method
Instrument: Micromass Platform II
Ionisation Mode: Electrospray+ve
Range: 100–1000 amu
Column: 50 mm ×2.1 mm Phenomenex Luna C18, 5 um.
Flow: 1.0 ml/min
Inj Vol: 5 ul
Diode Array Detector: 220–300 nm
Mobile Phase: A-Water+0.05% v/v TFA.

B-Acetonitrile+0.05% v/v TFA
Gradient: Time % A % B
0 100 0
8 5 95
8.1 100 0

It is to be understood that the present invention covers all combinations of particular and preferred subgroups described hereinabove.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of composition, process, or use claims and may include by way of example and without limitation the following claims.

The invention claimed is:

1. A compound of formula (I):

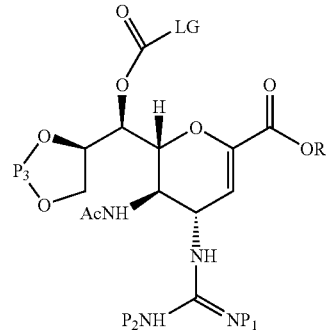

(I)

wherein R represents a carboxylic acid protecting group;
P$_1$ and P$_2$ can be the same or different and are selected from amine protecting groups;
P$_3$ represents a protecting group for 1,2 diols; and
LG represents a leaving group selected from the group consisting of para-nitrophenol, halide, imidazole and N-hydroxysuccinimide.

2. A compound according to claim 1, wherein R is C$_{1-6}$ alkyl or diphenylmethane.

3. A compound according to claim 1, wherein P$_1$ and/or P$_2$ is/are a t-butoxy carbonyl (Boc) group.

4. A compound according to claim 2, wherein $P_1$ and/or $P_2$ is/are a t-butoxy carbonyl (Boc) group.

5. A compound according to claim 1, wherein $P_3$ is CO or CHMe.

6. A compound according to claim 2, wherein $P_3$ is CO or CHMe.

7. A compound according to claim 3, wherein $P_3$ is CO or CHMe.

8. A compound according to claim 4, wherein $P_3$ is CO or CHMe.

9. A compound according to claim 1, wherein R is methyl or diphenylmethane, $P_1$ and $P_2$ are Boc, $P_3$ is CO and LG is para-nitrophenol.

10. A compound according to claim 2, wherein R is methyl or diphenylmethane, $P_1$ and $P_2$ are Boc, $P_3$ is CO and LG is para-nitrophenol.

11. A compound according to claim 3, wherein R is methyl or diphenylmethane, $P_1$ and $P_2$ are Boc, $P_3$ is CO and LG is para-nitrophenol.

12. A compound according to claim 4, wherein R is methyl or diphenylmethane, $P_1$ and $P_2$ are Boc, $P_3$ is CO and LG is para-nitrophenol.

13. A compound according to claim 5, wherein R is methyl or diphenylmethane, $P_1$ and $P_2$ are Boc, $P_3$ is CO and LG is para-nitrophenol.

14. A compound according to claim 6, wherein R is methyl or diphenylmethane, $P_1$ and $P_2$ are Boc, $P_3$ is CO and LG is para-nitrophenol.

15. A compound according to claim 7, wherein R is methyl or diphenylmethane, $P_1$ and $P_2$ are Boc, $P_3$ is CO and LG is para-nitrophenol.

16. A compound according to claim 8, wherein R is methyl or diphenylmethane, $P_1$ and $P_2$ are Boc, $P_3$ is CO and LG is para-nitrophenol.

17. A compound according to claim 1 wherein R is methyl or diphenylmethane, $P_1$ and $P_2$ are Boc, $P_3$ is CO and LG is para-nitrophenol.

18. A compound according to claim 2, wherein R is methyl or diphenylmethane, $P_1$ and $P_2$ are Boc, $P_3$ is CO and LG is para-nitrophenol.

19. A compound according to claim 14, wherein R is methyl or diphenylmethane, $P_1$ and $P_2$ are Boc, $P_3$ is CO and LG is para-nitrophenol.

20. A compound according to claim 15, wherein R is methyl or diphenylmethane, $P_1$ and $P_2$ are Boc, $P_3$ is CO and LO is para-nitrophenol.

21. A compound according to claim 16, wherein R is methyl or diphenylmethane, $P_1$ and $P_2$ are Boc, $P_3$ is CO and LO is para-nitrophenol.

22. A compound according to claim 17, wherein R is methyl or diphenylmethane, $P_1$ and $P_2$ are Boc, $P_3$ is CO and LO is para-nitrophenol.

23. A compound according to claim 18, wherein R is methyl or diphenylmethane, $P_1$ and $P_2$ are Boc, $P_3$ is CO and LO is para-nitrophenol.

24. A compound according to claim 19, wherein R is methyl or diphenylmethane, $P_1$ and $P_2$ are Boc, $P_3$ is CO and LO is para-nitrophenol.

25. A process for the preparation of a compound of formula (I) as defined in any one of claims 1 to 2 and 3 to 24, which comprises reacting a compound of formula (III);

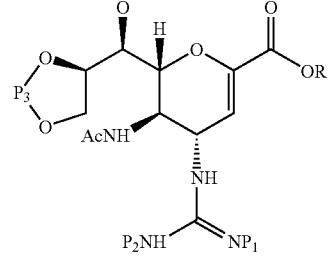

wherein $P_1$, $P_2$, $P_3$ and R are as defined in any one of claims 1 to 2 and 3 to 24, with a compound of formula (II);

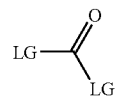

wherein each LG is as defined in any one of claims 1 to 2 and 3 to 24, in a solvent, and a base.

26. A process as claimed in claim 25, wherein the reaction is carried out in the absence of water.

27. A process according to claim 25, wherein the solvent is pyridine or a pyridine type solvent.

28. A process according to claim 25, wherein the base is a tertiary amine.

29. A process according to claim 28, wherein the tertiary amine is dimethylaminopyridine (DMAP), 4-pyrrolidinopyridine or 1,8-diazabicyclo[5.4.0] undec-7-ene.

30. A process according to claim 26, wherein the solvent is pyridine or a pyridine type solvent.

31. A process according to claim 26, wherein the base is a tertiary amine.

32. A process according to claim 27, wherein the base is a tertiary amine.

33. A process according to claim 30, wherein the base is a tertiary amine.

34. A process according to claim 31, wherein the tertiary amine is dimethylaminopyridine (DMAP), 4-pyrrolidinopyridine or 1,8-diazabicyclo[5.4.0] undec-7-ene.

35. A process according to claim 32, wherein the tertiary amine is dimethylaminopyridine (DMAP), 4-pyrrolidinopyridine or 1,8-diazabicyclo[5.4.0] undec-7-ene.

36. A process according to claim 33, wherein the tertiary amine is dimethylaminopyridine (DMAP), 4-pyrrolidinopyridine or 1,8-diazabicyclo[5.4.0] undec-7-ene.

* * * * *

UNITED STATES PATENT AND TRADEMARK OFFICE
CERTIFICATE OF CORRECTION

| | |
|---|---|
| PATENT NO. | : 7,230,114 B2 |
| APPLICATION NO. | : 10/488791 |
| DATED | : June 12, 2007 |
| INVENTOR(S) | : Brian David Judkins et al. |

It is certified that error appears in the above-identified patent and that said Letters Patent is hereby corrected as shown below:

In Column 6, Line 50: Please delete "was stirred at 22° C. For 17" and replace with -- was stirred at 22° C for 17 --.

In Column 7, Line 43: Please delete "(acetylamino)4-amino" and replace with -- (acetylamino)-4-amino --.

In Column 10, Line 9: Please delete "was stirred at 22° C. For 17" and replace with -- was stirred at 22° C for 17 --.

In Column 11, Line 20: Please delete "(acetylamino)$_4$-" and replace with -- (acetylamino)-4-amino- --.

In Column 11, Line 63: Please delete "C18, 5 um" and replace with -- C18, 5 μM --.

In Column 11, Line 65: Please delete "Vol: 5 ul" and replace with -- Vol: 5 μl --.

In Column 12, Lines 21, 22, 23, and 24: Please delete

"Gradient: Time % A % B 0 100 0

8 5 95

8.1 100 0"

UNITED STATES PATENT AND TRADEMARK OFFICE
CERTIFICATE OF CORRECTION

PATENT NO. : 7,230,114 B2
APPLICATION NO. : 10/488791
DATED : June 12, 2007
INVENTOR(S) : Brian David Judkins et al.

It is certified that error appears in the above-identified patent and that said Letters Patent is hereby corrected as shown below:

and replace with

| -- Gradient: | Time | %A | %B |
|---|---|---|---|
| | 0 | 100 | 0 |
| | 8 | 5 | 95 |
| | 8.1 | 100 | 0 --. |

IN THE CLAIMS

In Columns 13 and 14: Please delete claims 20-24, which are identical in scope to claims 15 - 19.

In Column 14, Claim 25, Formula (III): please delete:

" 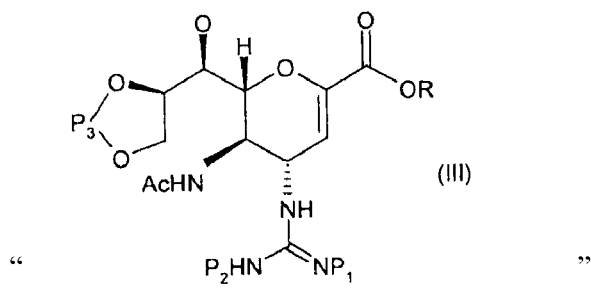 "

UNITED STATES PATENT AND TRADEMARK OFFICE
CERTIFICATE OF CORRECTION

PATENT NO. : 7,230,114 B2
APPLICATION NO. : 10/488791
DATED : June 12, 2007
INVENTOR(S) : Brian David Judkins et al.

It is certified that error appears in the above-identified patent and that said Letters Patent is hereby corrected as shown below:

and replace with:

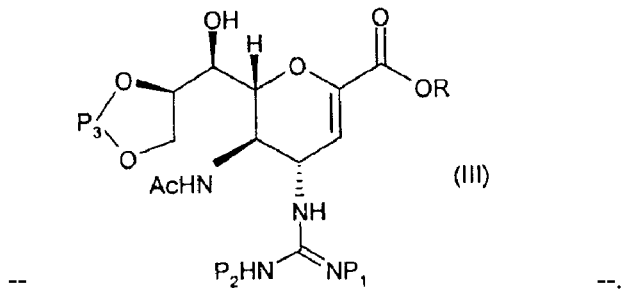

-- -- .

Signed and Sealed this

Twenty-eighth Day of October, 2008

JON W. DUDAS
*Director of the United States Patent and Trademark Office*